(12) United States Patent
Nye

(10) Patent No.: US 7,375,628 B2
(45) Date of Patent: May 20, 2008

(54) MESSAGE TRANSMISSION IN ONE OR MORE LANGUAGES BASED ON ONE OR MORE PERSONAL INFORMATION COMPONENT INPUTS

(75) Inventor: Robert Alan Nye, Plainfield, IL (US)

(73) Assignee: Lucent Technologies Inc., Murray Hill, NJ (US)

( * ) Notice: Subject to any disclaimer, the term of this patent is extended or adjusted under 35 U.S.C. 154(b) by 395 days.

(21) Appl. No.: 10/852,879

(22) Filed: May 25, 2004

(65) Prior Publication Data

US 2005/0267736 A1    Dec. 1, 2005

(51) Int. Cl.
*G08B 1/08* (2006.01)
*G08B 13/14* (2006.01)
*H04M 1/725* (2006.01)
*H04M 3/42* (2006.01)
*G06F 17/20* (2006.01)
*G06F 17/28* (2006.01)

(52) U.S. Cl. ............ 340/506; 340/539.1; 340/384.1; 340/571; 340/692; 455/412.1; 455/412.2; 455/414.1; 455/566; 455/18; 704/1; 704/2; 704/8; 704/9; 704/270.1

(58) Field of Classification Search ........... 340/539.1, 340/384.1, 571, 328, 692; 455/414.1, 566, 455/18, 412.1, 412.2, 414.2; 704/1, 2, 8, 704/9
See application file for complete search history.

(56) References Cited

U.S. PATENT DOCUMENTS

| | | | | |
|---|---|---|---|---|
| 5,020,155 | A * | 5/1991 | Griffin et al. | 398/130 |
| 5,152,003 | A * | 9/1992 | Poch | 455/18 |
| 5,796,328 | A * | 8/1998 | Golant | 340/384.1 |
| 6,169,498 | B1 * | 1/2001 | King et al. | 340/686.1 |
| 6,956,831 | B1 * | 10/2005 | Mahr | 370/310 |
| 7,221,933 | B2 * | 5/2007 | Sauer et al. | 455/412.1 |
| 2004/0198326 | A1 * | 10/2004 | Hirani | 455/414.1 |
| 2004/0236579 | A1 * | 11/2004 | Cardenes et al. | 704/270.1 |

\* cited by examiner

*Primary Examiner*—Jeffery Hofsass
*Assistant Examiner*—Lam Pham

(57) ABSTRACT

An information component of an apparatus in one example selects one or more languages for transmission of one or more messages to one or more personal information components based on one or more inputs from one or more of the one or more personal information components.

14 Claims, 4 Drawing Sheets

MESSAGE TRANSMISSION IN ONE OR MORE LANGUAGES BASED ON ONE OR MORE PERSONAL INFORMATION COMPONENT INPUTS

TECHNICAL FIELD

The invention relates generally to providing information to a user and more particularly to providing information to the user in a format recognizable to the user.

BACKGROUND

Braille signs are located in close proximity to signs, for example, exit signs, in order to provide information to visually impaired individuals. Braille consists of varied arrangements of raised dots representing letters and numerals. The visually impaired individual locates the Braille sign and then identifies the letters and numerals by touch. Where the visually impaired individual is unfamiliar with the location of the Braille sign, for example, the visually impaired individual is unfamiliar with the area, the visually impaired individual is unable to obtain the information provided by the Braille sign. As another shortcoming, the raised dots that represent the letters and numerals tend to wear down after years of use. As the raised dots wear down the visually impaired individual is unable to obtain the information from the Braille sign.

In addition, the signs provide the information in one or more written languages. For example, the signs provide a set of messages written in English, the same set of messages written in French, and the same set of messages written in Spanish. As yet another shortcoming, an individual that is unfamiliar with written English, French, and Spanish is unable to interpret the signs to obtain the information provided by the signs.

Thus, a need exists for identifying when an individual is spatially near one or more signs. A further need exists for notifying the individual of the information on the signs when the individual is spatially near the signs. Yet a further need exists for providing the information on the signs to the individual in one or more languages understandable by the individual.

SUMMARY

In one embodiment, there is provided an apparatus comprising an information component that selects one or more languages for transmission of one or more messages to one or more personal information components based on one or more inputs from one or more of the one or more personal information components.

In one embodiment, there is provided a method for receiving one or more inputs from one or more personal information components and transmitting one or more messages in one or more languages to one or more of the one or more personal information components.

DESCRIPTION OF THE DRAWINGS

Features of exemplary implementations of the invention will become apparent from the description, the claims, and the accompanying drawings in which:

DETAILED DESCRIPTION

Figure 1:
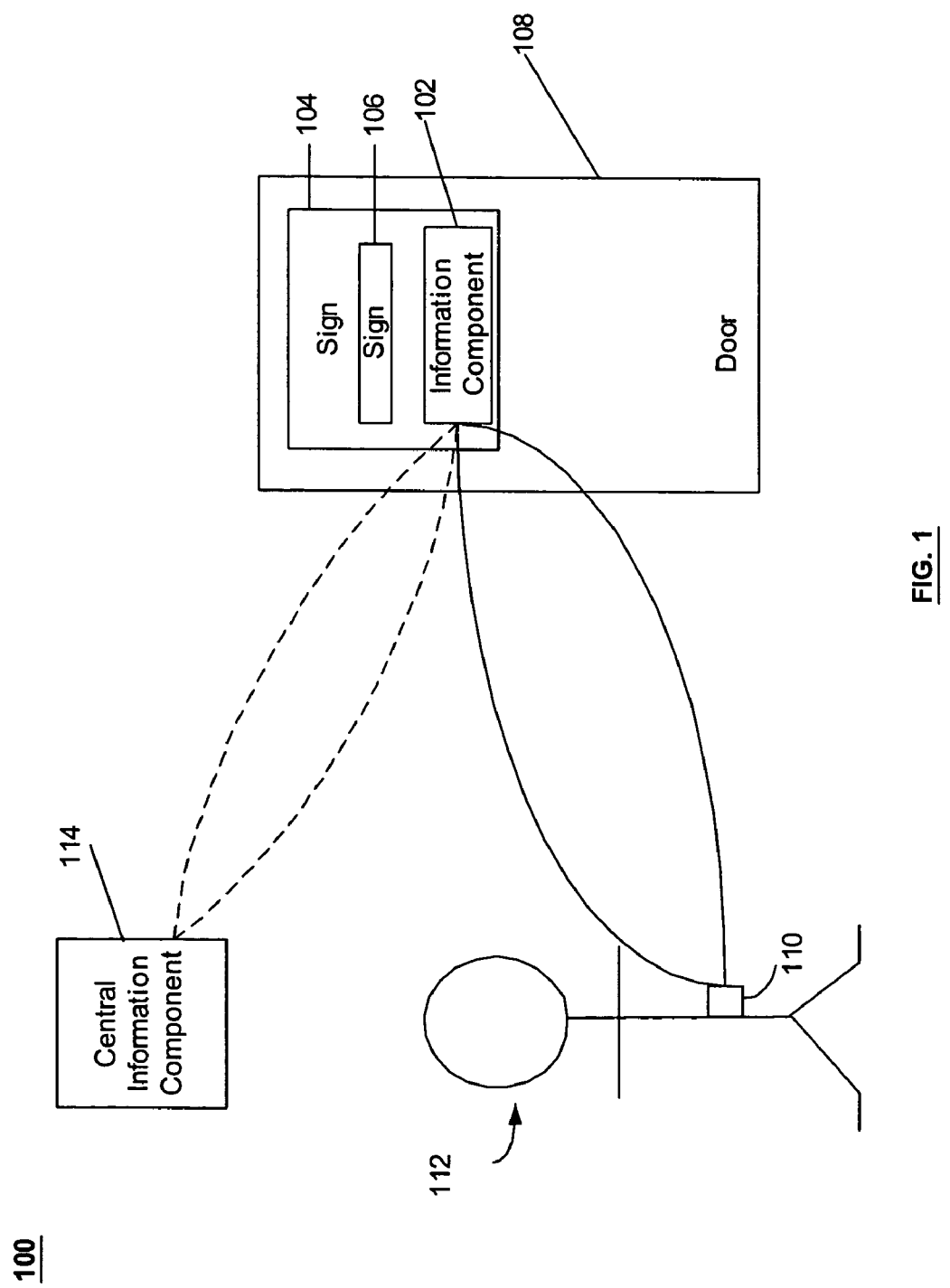
FIG. 1 is a representation of one or more information components, one or more signs, one or more doors, one or more personal information components, and one or more users of the personal information components.

Turning to FIG. 1, an apparatus 100 in one example comprises one or more information components 102, one or more signs 104 and 106, one or more doors 108, one or more personal information components 110, one or more users 112 of the personal information component 110, and one or more central information components 114. The information component 102 and the signs 104 and 106 in one example are located on the door 108. In one example, the information component 102 is embedded in the sign 104. In another example, the information component 102 is embedded in the sign 106. In yet another example, the information component 102 is embedded within the door 108. The sign 104 comprises one or more messages in a first language, for example, Spanish. The sign 106 comprises the one or more messages of the sign 104 in a second language, for example, Braille. The information component 102 and the personal information component 110 cooperate to aurally provide the one or more messages of the signs 104 and/or 106 to the user 112 of the personal information component 110. In one example, the information component 102 and the central information component 114 cooperate to update one or more of the one or more messages. In another example, the information component 102 and the central information component 114 cooperate to provide one or more emergency messages to the user 112 of the personal information component 110.

The personal receiver component 110 allows the user 112 of the personal information component 110 to select a language in which to receive one or more messages from the information component 102. The personal receiver component 110 sends as output, one or more requests for one or more messages in the language. The personal receiver component 110 receives the messages in the language from the information component 102. The personal receiver component 110 makes audible the one or more messages for the user 112 of the personal information component 110.

In one example, the central information component 114 allows for initiation of one or more message notifications to the information component 102. The information component 102 updates one or more of the one or more messages stored in the information component 102 in response to the one or more message notifications. In another example, the central information component 114 sends one or more notifications of one or more emergency situations, for example, fire, flood, or biological attack, to the information component 102. For example, the central information component 114 communicates with an emergency system of a building. Upon occurrence of an emergency situation, the central information component 114 receives a notification from the fire system. The central information component 114 sends one or more portions of an escape route to the information component 102. The information component 102 transmits the one or more portions of the escape route to the personal information component 110.

Figure 2:
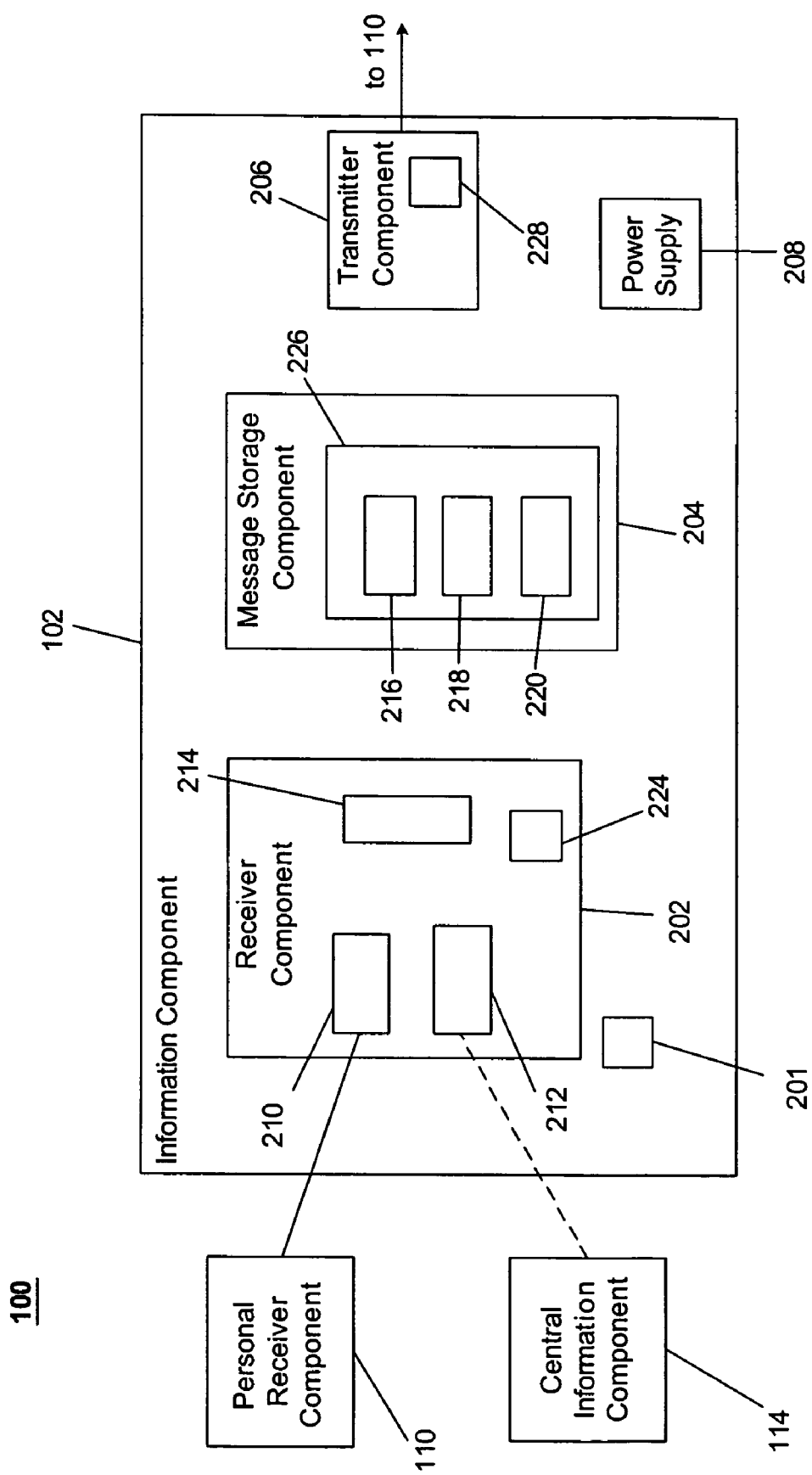
FIG. 2 is a representation of one or more receiver components, one or more message storage components, one or more transmitter components, and one or more power supplies of the information component of the apparatus of FIG. 1.

Turning to FIG. 2, the information component 102 in one example comprises one or more identification tags 201, one or more receiver components 202, one or more message storage components 204, one or more transmitter components 206, and one or more power supplies 208. The information component 102 is addressed by the identification tag 201. For example, the information component 102 employs the identification tag 201 to respond to one or more message notifications that comprise the identification tag 201. The receiver component 202 receives one or more inputs from the personal information component 110 and one or more message notifications from the central information component 114. The message storage component 204 stores one or more available messages in one or more available languages, for example, languages 216, 218 and 220. The receiver component 202 and the message storage component 204 cooperate to select a language for transmission of one or more messages to the personal information component 110. The message storage component 204 provides the one or more messages in the language to the transmitter component 206. The transmitter component 206 sends the one or more messages in the language to the personal information component 110. The receiver component 202 and the transmitter component 206 in one example employ one or more wireless protocols, for example, an 802.11 protocol, to communicate with the personal information component 110 and/or the central information component 114.

The receiver component 202 comprises one or more wireless receiver components 210, one or more central information receiver components 212, one or more message update interface components 214, and an instance of a recordable data storage medium 224, as described herein. The wireless receiver component 210 in one example comprises a receiver. The wireless receiver component 210 in one example receives data on multiple channels. The wireless receiver component 210 employs one or more channels to receive as input, one or more requests for one or more messages in a language from the personal information component 110, as will be appreciated by those skilled in the art. In one example, the input comprises one or more language identifiers. The language identifier indicates a language for transmission of one or more messages to the personal information component 110 for the user 112. In another example, the input comprises one or more type identifiers. The type identifier indicates a type of message for which the user 112 desires to receive. The wireless receiver component 210 provides the inputs to the message update interface component 214.

The central information receiver component 212 in one example comprises a receiver. The central information receiver component 212 in one example employs one or more audio compression technologies, for example, a Moving Pictures Experts Group Audio Layer 3 ("MP3") audio compression technology, to decompress the one or more messages from the central information component 114. The central information receiver component 212 employs one or more wireless technologies to receive the one or more messages from the central information component 114.

The central information receiver component 212 employs one or more channels to receive one or more message notifications and/or one or notifications of one or more emergency situations from the central information component 114. The central information receiver component 212 employs the identification tag 201 to respond to one or more of the message notifications and/or one or more of the notifications of the emergency situations. For example, the central information component 114 inserts an identification tag into a message notification. Upon receipt of the message notification, the central information receiver component 212 compares the identification tag of the message notification to the identification tag 201 of the information component 102. Where the identification tag of the message notification matches the identification tag 201 of the information component 102, the central information receiver component 212 responds to the message notification. The central information receiver component 212 provides the message notifications and/or the notifications of the emergency situations to the message update interface component 214.

The message update interface component 214 in one example performs a selection between the inputs from the personal receiver component 110 and the message notifications and/or the notifications of the emergency situations from the central information component 114. The message update interface component 214 in one example employs a priority scheme to perform the selection. In one example, the message update interface component 214 selects the message notifications based on the priority scheme. In another example, the message update interface component 214 selects the notifications of the emergency situations based on the priority scheme. The message update interface component 214 provides the selection to the message storage component 204.

The message storage component 204 stores the one or more available messages in the one or more available languages. The message storage component 204 stores one or more messages in the language 216, the one or more messages in the language 218, and the one or more messages in the language 220. The languages 216, 218 and 220 in one example comprise English, French and Spanish, respectively. The message storage component 204 comprises an instance of a recordable data storage medium 226, as described herein. In one example, the message storage component 204 employs the selection provided by the message update interface component 214 to select a language of the available languages for transmission of one or more messages from one or more available messages. In another example, the message storage component 204 employs the selection provided by the message update interface component 214 to select a type of message of the available messages for transmission of one or more messages from the available messages.

For example, the message storage component 204 employs a language identifier to select the language 216 from the languages 214, 216 and 218, for transmission of one or more messages. Where the message storage component 204 determines that the language identifier is associated with an unavailable language (i.e., a language that is unsupported by the information component 102) the message storage component 204 selects a default language for transmission of one or more messages to the personal information component 110. For example, the user 112 of the personal information component 110 selects Italian as the language in which to receive one or more messages associated with the sign 104 of the door 108. The message storage component 204 determines that Italian is an unavailable language and selects English as the default language. The message storage component 204 selects English for transmission of the one or more messages to the personal information component 110. The message storage component 206 provides one or more messages in a language to the transmitter component 206 for transmission to the personal information component 110.

In another example, the message storage component 204 stores one or more messages in one or more types in one or more languages. The types of messages in one example comprise one or more: age appropriate messages, emergency messages, tourist messages, and/or directional messages such as locations of doorways, stairwells, and elevators. For example, the message storage component 204 stores one or more messages for children in English, one or more messages for teens in English, and one or more messages for adults in English. The message storage component 204 employs the selection provided by the message update interface component 214 to select one or more messages of a type of message to transmit to the personal information component 110. For example, the message storage component 204 selects for transmission, the one or more messages for adults in English to transmit to the personal information component 110. In another example, the message storage component 204 selects one or more messages of the tourist message type of message to transmit to the personal information component 110.

In yet another example, the message storage component 204 employs the selection provided by the message update interface component 214 to update one or more of the one or more available messages. In one example, the door 108 is out of order. The central information component 114 initiates one or more message notifications to update one or more messages stored in the information component 102 to indicate that the door 108 is out of order. In another example, the central information component 114 initiates one or more message notifications to update the one or more messages to indicate that a fire is behind the door 108. The message storage component 204 provides the one or more messages to the transmitter component 206.

The transmitter component 206 transmits the one or more messages in the one or more languages to the personal information component 110. The transmitter component 206 employs one or more channels to transmit the on or more messages to the message storage component 204. The transmitter component 206 in one example comprises one or more transmitters and an instance of a recordable data storage medium 228, as described herein. The transmitters in one example comprise one or more short range transmitters, as will be appreciated by those skilled in the art. The transmitter component 206 transmits the one or more messages to the personal information component 110, where the personal information component 110 is located within a limited spatial distance relative to the information component 102. The limited spatial distance in one example comprises about one to five meters.

The power supply 208 provides power to the receiver component 202, the message storage component 204, and the transmitter component 206. The power supply 208 in one example comprises an uninterruptible power supply ("UPS") to continue supplying power to the receiver component 202, the message storage component 204, and the transmitter component 206 in the event of a power loss.

Figure 3:
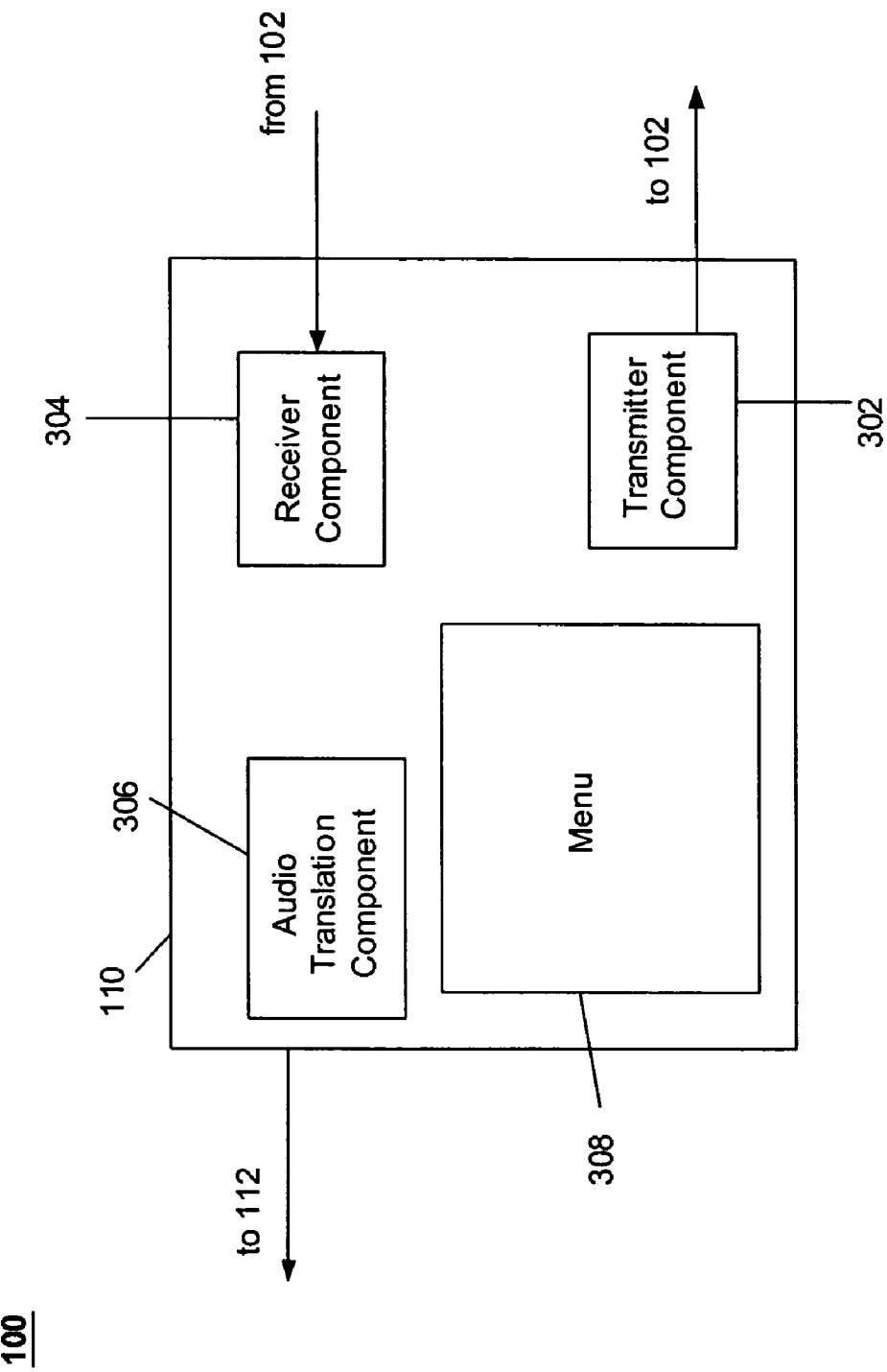
FIG. 3 is a representation of one or more transmitter components, one or more receiver components, one or more audio translation components, and one or more menus of the personal information component of the apparatus of FIG. 1.

Turning to FIG. 3, the personal information component 110 comprises one or more transmitter components 302, one or more receiver components 304, one or more audio translation components 306, and one or more menus 308. The transmitter component 302 in one example comprises a transmitter that continuously transmits as output, one or more requests for one or more messages in one or more languages selected by the user 112. The receiver component 304 in one example comprises a wireless receiver. The audio translation component 306 in one example performs one or more digital to analogue conversions to make audible the one or more messages in the language received from the information component 102. The audio translation component 306 in one example cooperates with an internal, an external speaker of the personal information component, or a pair of headphones to audibly provide the messages to the user 112. The menu component 308 in one example comprises a Graphical User Interface ("GUI").

The menu component 308 comprises a language selection component 310 and a message type selection component 312. In one example, the user 112 of the personal information component 110 employs the language selection component 310 of the menu 308 to choose a language of a plurality of languages in which to hear the one or more messages. In another example, the user 112 of the personal information component 110 employs the message type selection component 312 of the menu 308 to choose a type of message to receive. In one example, the user 112 chooses to receive messages of an emergency type. In another example, the user 112 chooses to receive messages of a tourist type. In yet another example, the user 112 chooses to receive messages of a directional type such as messages regarding doorways, stairwells, and elevators. The personal information component 110 in one example comprises an MPEG Audio Player 3 ("MP3 player").

The user 112 employs the menu 308 to indicate the language from the plurality of languages. The menu 308 provides the indication of the language to the transmitter component 302. The transmitter component 302 in one example provides a language identifier associated with the language within a request to the information component 102 for the one or more messages in the language. The receiver component 304 in one example receives one or more messages from the information component 102. The receiver component 304 provides the one or more messages to the audio translation component 306.

An illustrative description of exemplary operation of the apparatus 100 is presented, for explanatory purposes. The user 112 is a native English speaker and does not speak nor read Spanish. The user 112 travels to Spain. The user 112 employs the menu 308 of the personal information component 110 to select English as the language in which to receive one or more messages. The personal information component 110 continuously transmits as an output, one or more requests to receive one or more messages in English. The user 112 encounters the sign 104, indicating the presence of an exit door, for example, the door 108. The information component 102 associated with the door 108 receives as input, the request to receive the one or more messages in English from the personal information component 110. The information component 102 selects English for transmission of the one or more messages. The information component 102 transmits the messages in English to the personal information component 110. The personal information component 110 makes audible the messages in English for the user 112. The user 112 employs a pair of headphones to hear the messages in English.

Figure 4:
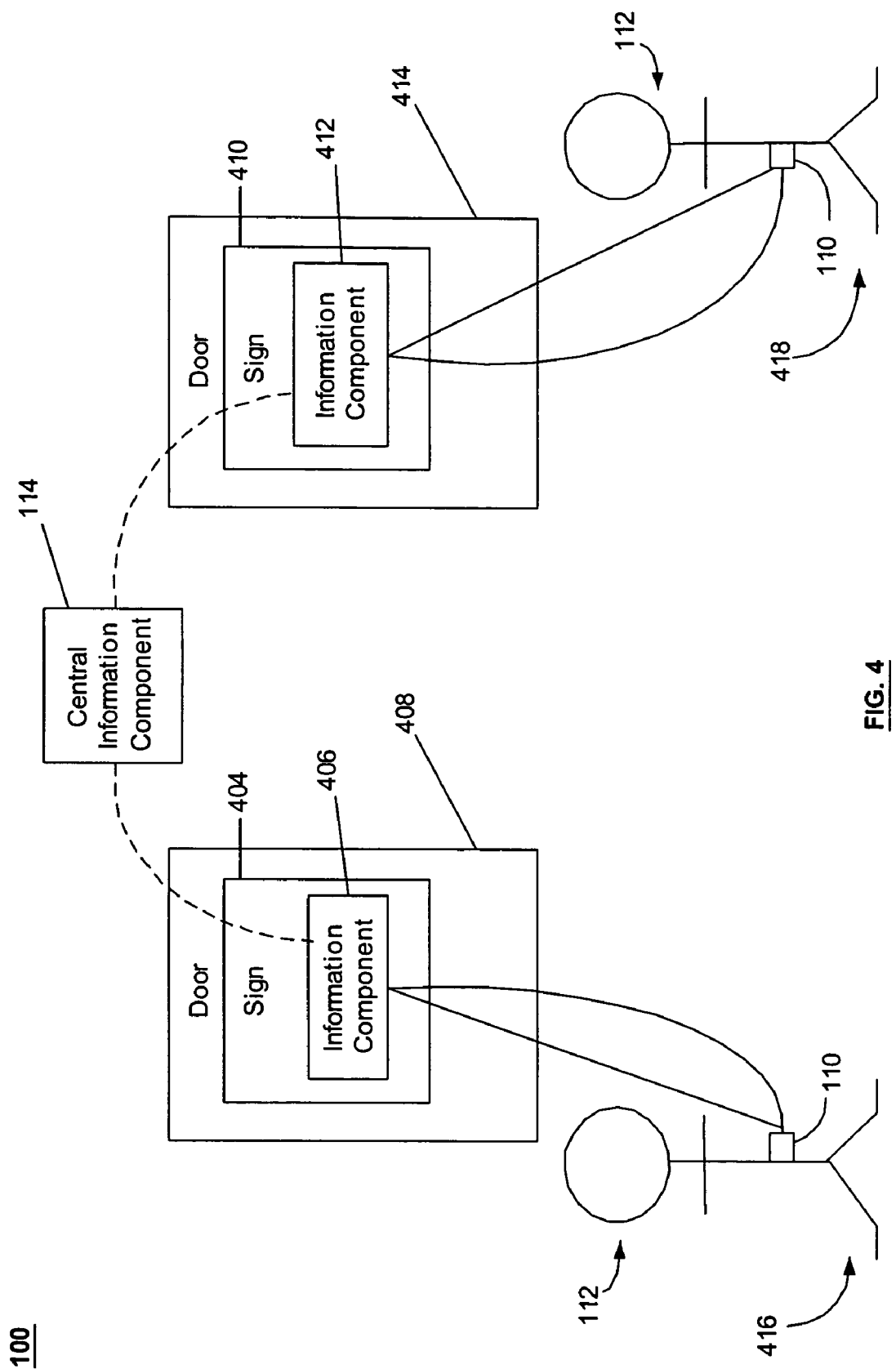
FIG. 4 is a representation of an exemplary operation of the apparatus of FIG. 1.

Turning to FIG. 4, in another illustrative description of exemplary operation of the apparatus 100, the user 112 speaks Spanish and is visually impaired. The user 112 enters an unfamiliar building that comprises doors 408 and 414. The personal information component 110 continuously sends as output, one or more requests for one or more directional messages in Spanish. The user 112 enters a first limited spatial distance 416 relative to the door 408, an information component 406 transmits a first one or more messages to the personal information component 110. The user 112 exits the first limited spatial distance 416 of the door 108. Where the user 112 enters a second limited spatial distance 418 relative to the door 414, an information component 412 transmits a second one or more messages to the personal information component 110.

In yet another illustrative description of exemplary operation of the apparatus 100, the user 112 selects to receive one or more tourist messages in Spanish. The personal information component 110 continuously sends one or more requests for the tourist messages in English. The user 112 enters the first limited spatial distance 416 relative to the door 408. A bombing occurs in an area close to the door 408. The central information component 114 sends an emergency notification for the bombing to the information components 406 and 412. The information component 406 transmits one or more first portions of an escape path in Spanish to the personal information component 110. As the user 112 enters the second limited spatial distance 418 relative to the door 414, the information component 412 transmits one or more second portions of the escape path in Spanish to the personal information component 110.

The apparatus 100 in one example comprises a plurality of components such as one or more of electronic components, hardware components, and computer software components. A number of such components can be combined or divided in the apparatus 100. An exemplary component of the apparatus 100 employs and/or comprises a set and/or series of computer instructions written in or implemented with any of a number of programming languages, as will be appreciated by those skilled in the art. The apparatus 100 in one example comprises any (e.g., horizontal, oblique, or vertical) orientation, with the description and figures herein illustrating one exemplary orientation of the apparatus 100, for explanatory purposes.

The apparatus 100 in one example employs one or more computer-readable signal-bearing media. Examples of a computer-readable signal-bearing medium for the apparatus 100 comprise the recordable data storage medium 224 of the receiver component 202, the recordable data storage medium 226 of the message storage component 204, and the recordable data storage medium 228 of the transmitter component 208. For example, the computer-readable signal-bearing medium for the apparatus 100 comprises one or more of a magnetic, electrical, optical, biological, and atomic data storage medium. In one example, the computer-readable signal-bearing medium comprises a modulated carrier signal transmitted over a network comprising or coupled with the apparatus 100, for instance, one or more of a telephone network, a local area network ("LAN"), the internet, and a wireless network.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

We claim:
1. An apparatus, comprising:
an information component that selects one or more spoken languages for transmission of one or more messages to one or more personal information components based on one or more inputs from one or more of the one or more personal information components, wherein the information component receives the one or more inputs from the one or more of the one or more personal information components, wherein the information component employs the one or more inputs from the one or more of the one or more personal information components to select the one or more messages from one or more available messages for transmission to the one or more personal information components; wherein the selected one or more messages comprise instructional and guidance messages; and
the one or more inputs from the one or more of the one or more personal information components comprise one or more message type identifiers, wherein the information component employs one or more of the one or more type identifiers to select the one or more messages having selected languages from the one or more available messages.

2. The apparatus of claim 1, wherein the one or more inputs from the one or more of the one or more personal information components comprise one or more language identifiers, wherein the information component employs one or more of the one or more language identifiers to select the one or more languages from one or more available languages.

3. The apparatus of claim 2, wherein the one or more inputs from the one or more of the one or more personal information components comprise an input from a personal information component, wherein the input comprises a language identifier, wherein the language identifier is associated with a first language;
wherein the information component determines that the first language comprises an unavailable language;
wherein the information component selects a second language from the one or more available languages for transmission of the one or more messages to the one or more personal information components.

4. The apparatus of claim 1, wherein the one or more inputs from the one or more of the one or more personal information components comprise an input from a personal information component;
wherein the personal information component allows for selection of a first language for transmission of the one or more messages;
wherein the personal information component sends as an output, a request for transmission of the one or more messages to the one or more personal information components in the first language;
wherein the information component receives as input, the request for transmission of the one or more messages to the one or more personal information components in the first language;
wherein the information component selects a second language from one or more available languages for transmission of the one or more messages to the one or more personal information components.

5. The apparatus of claim 1, wherein the information component comprises one or more transmitter components that sends a first one or more of the one or more messages to a first one or more of the one or more personal information components and a second one or more of the one or more messages to a second one or more of the one or more personal information components.

6. The apparatus of claim 1, wherein the one or more messages comprise one or more age appropriate messages, wherein the information component employs the one or more of the one or more type identifiers to select the one or more age appropriate messages from the one or more available messages for transmission to the one or more personal information components.

7. The apparatus of claim 1, wherein the information component receives the one or more inputs from the one or more of the one or more personal components;
wherein the information component employs one or more transmitter components to transmit the one or more messages to the one or more personal information components, wherein the one or more personal information components &e located within a limited spatial distance relative to the information component.

8. An apparatus, comprising:
an information component that selects one or more spoken languages for transmission of one or more messages to one or more personal information components based on one or more inputs from one or more of the one or more personal information components; wherein the information component receives the one or more inputs from the one or more of the one or more personal information components and the selected one or more messages comprise instructional and guidance messages;
a plurality of information components having the information component;
a central information component that sends one or more message notifications to one or more of the plurality of information components;
wherein the one or more of the plurality of information components update one or more of one or more available messages based on one or more of the one or more message notifications.

9. The apparatus of claim 8, wherein the plurality of information components are identified by a plurality of identification tags;
wherein the central information component employs one or more of the plurality of identification tags to send the one or more message notifications to the one or more of the plurality of information components;
wherein one or more of the one or more of the plurality of information components employ the one or more of the plurality of identification tags to respond to the one or more message notifications.

10. An apparatus, comprising:
an information component that selects one or more spoken languages for transmission of one or more messages to one or more personal information components based on one or more inputs from one or more of the one or more personal information components;
wherein the one or more messages comprise one or more emergency messages;
wherein the information component selects the one or more languages for transmission of the one or more emergency messages to the one or more personal information components upon receipt of a notification of an emergency situation from a central information component;
the information component having a first information component, wherein a plurality of information components comprise the first information component and a second information component, wherein the one or more emergency messages comprise a first portion of an escape route;
wherein the first information component transmits the first portion of the escape route to the one or more personal information components;
wherein the second information component transmits a second portion of the escape route to the one or more personal information components.

11. The apparatus of claim 10, wherein the one or more personal information components comprise a personal information component;
wherein the first information component transmits the first portion of the escape route to the personal information component, wherein the personal information component is located at a first position that is within a first limited spatial distance relative to the first information component;
wherein the second information component transmits the second portion of the escape route to the personal information component, wherein the personal information component is located at a second location that is within a second limited spatial distance relative to the second information component.

12. A method, comprising:
selecting, by an information component, one or more spoken languages for transmission of one or more messages, the information component having one or more personal information components, based on one or more inputs from one or more of the one or more personal information component; wherein the information component receives the one or more inputs from the one or more of the one or more personal information components and the selected one or more messages comprise instructional and guidance messages;
receiving, by the information component, the one or more inputs from the one or more of the one or more personal information components;
employing, by the information component, the one or more inputs from the one or more of the one or more personal information components to select the one or more messages from one or more available messages for transmission to the one or more personal information components, the one or more inputs from the one or more of the one or more personal information components having one or more message type identifiers; and
employing, by the information component, one or more of the one or more type identifiers to select the one or more messages having selected languages from the one or more available messages.

13. The method of claim 12, wherein the one or more messages comprise one or more age appropriate messages, wherein the information component employs the one or more of the one or more type identifiers to select the one or more age appropriate messages from the one or more available messages for transmission to the one or more personal information components.

14. The method of claim 12, wherein the information component receives the one or more inputs from the one or more of the one or more personal components; and wherein the information component employs one or more transmitter components to transmit the one or more messages to the one or more personal information components, wherein the one or more personal information components are located within a limited spatial distance relative to the information component.

* * * * *